United States Patent [19]

Bauman

[11] Patent Number: 5,501,651
[45] Date of Patent: Mar. 26, 1996

[54] FLUID SUBMERSIBLE LARYNGOSCOPE PREVENTING ELECTROLYTIC CURRENT FLOW

[76] Inventor: Jack Bauman, 2210 Wilshire Blvd., Ste. 705, Santa Monica, Calif. 90403

[21] Appl. No.: 258,729

[22] Filed: Jun. 13, 1994

[51] Int. Cl.⁶ ................................. A61B 1/26
[52] U.S. Cl. .......................... 600/198; 600/199
[58] Field of Search ............ 128/10, 11; 600/185, 600/198, 199

[56] References Cited

U.S. PATENT DOCUMENTS

| | | |
|---|---|---|
| 2,289,226 | 7/1942 | Von Foregger. |
| 2,433,705 | 12/1947 | Palmeter. |
| 3,426,749 | 2/1969 | Jephcott. |
| 3,579,269 | 5/1971 | Ostensen. |
| 3,598,113 | 8/1971 | Moore. |
| 3,609,340 | 9/1971 | Habro. |
| 3,766,909 | 10/1973 | Ozbey. |
| 3,771,514 | 11/1973 | Huffman et al.. |
| 3,826,248 | 7/1974 | Gobels. |
| 4,037,588 | 7/1977 | Heckele. |
| 4,112,933 | 9/1978 | Moses. |
| 4,114,187 | 9/1978 | Uke. |
| 4,114,609 | 9/1978 | Moses. |
| 4,273,112 | 6/1981 | Heine et al.. |
| 4,295,465 | 10/1981 | Racz et al.. |
| 4,306,547 | 12/1981 | Lowell. |
| 4,314,551 | 2/2982 | Kadell. |
| 4,320,745 | 3/1982 | Bhitiyakul et al.. |
| 4,337,761 | 7/1982 | Upsher. |
| 4,384,570 | 5/1983 | Roberts. |
| 4,527,223 | 7/1985 | Maglica. |
| 4,557,256 | 12/1985 | Bauman. |
| 4,565,187 | 1/1986 | Soloway. |
| 4,570,614 | 2/1986 | Bauman. |
| 4,573,451 | 3/1986 | Bauman. |
| 4,579,108 | 4/1986 | Bauman. |
| 4,583,528 | 4/1986 | Bauman. |
| 4,592,343 | 6/1986 | Upsher. |
| 4,607,623 | 8/1986 | Bauman. |
| 4,679,547 | 7/1987 | Bauman. |
| 4,729,367 | 3/1988 | Bauman ........................ 128/11 |
| 4,815,451 | 3/1989 | Bauman ........................ 128/11 |
| 4,958,624 | 9/1990 | Stone et al. ................... 128/11 |
| 5,060,633 | 10/1991 | Gibson ......................... 128/11 |

*Primary Examiner*—Richard J. Apley
*Assistant Examiner*—John P. Leubecker
*Attorney, Agent, or Firm*—William W. Haefliger

[57] ABSTRACT

An improvement of a fluid submersible laryngoscope including a hollow handle to contain power supply means and a blade to be inserted into a patient's mouth includes a terminal pin carried on an end portion of the handle by a tubular elastomeric body and an insulation disc located between the power supply means and the end of the elastomeric body. The elastomeric body acts as a fluid sealing means to block access of external fluid into the hollow handle whether or not the blade is attached to the handle. The insulation disc defines a bore through which the terminal pin at least partially extends such that attachment of the blade to the handle will cause the terminal pin to move through the bore and contact the power supply means.

13 Claims, 3 Drawing Sheets

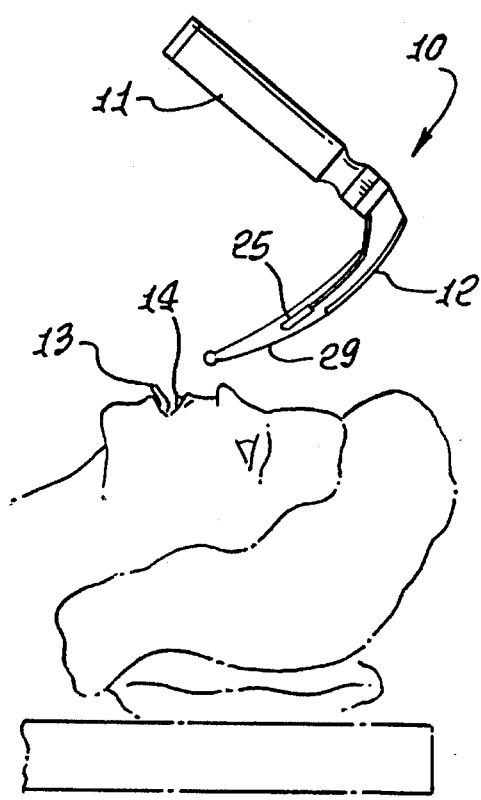
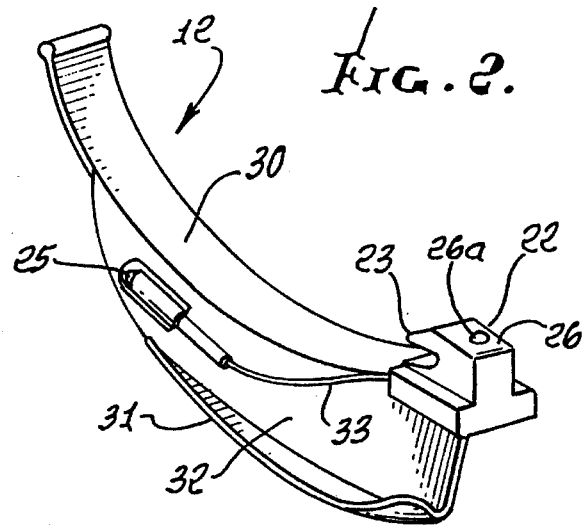
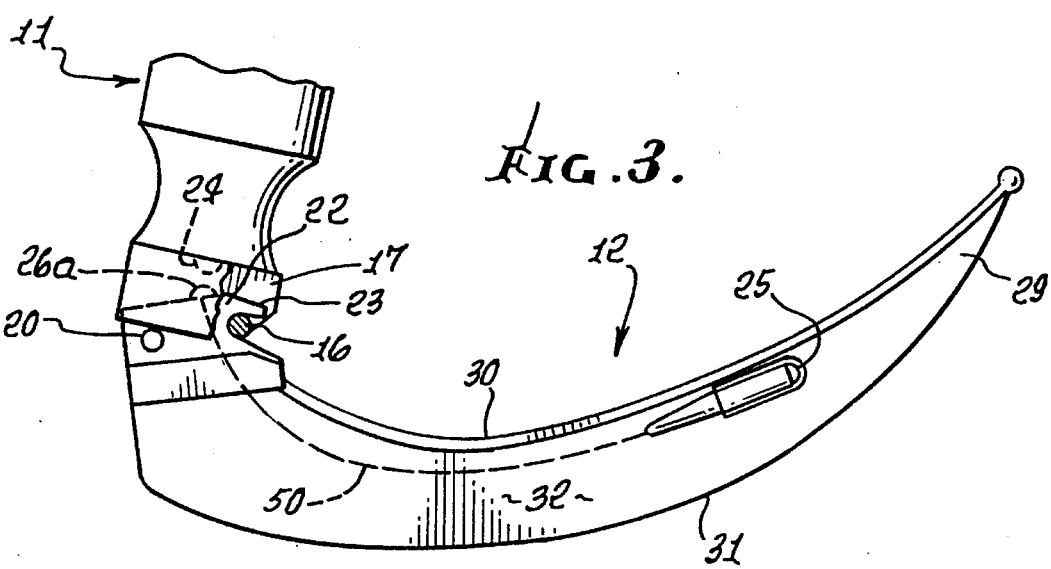

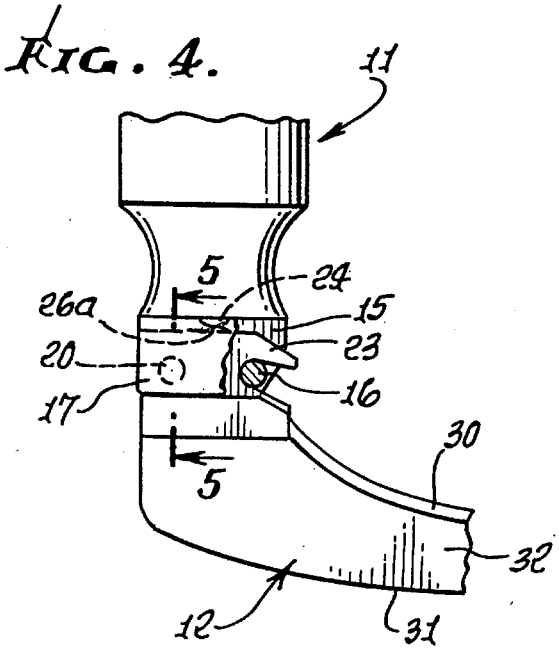
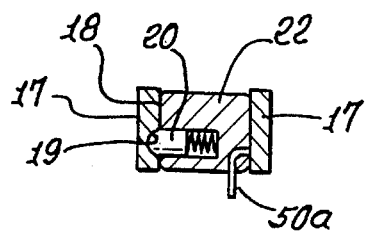
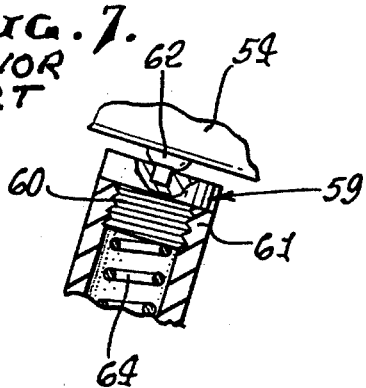
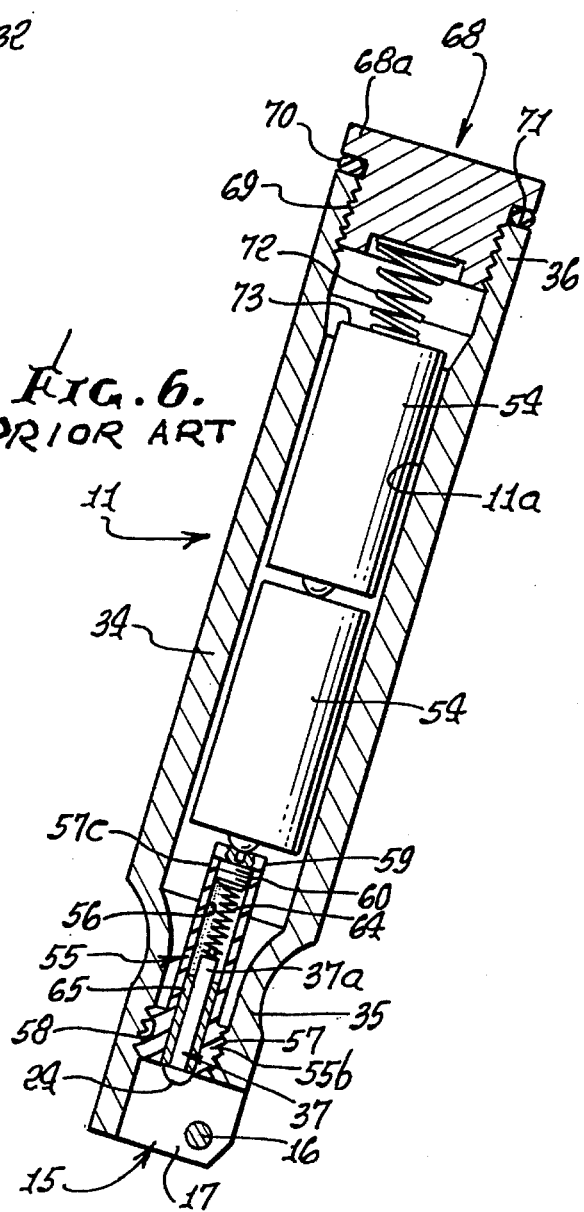

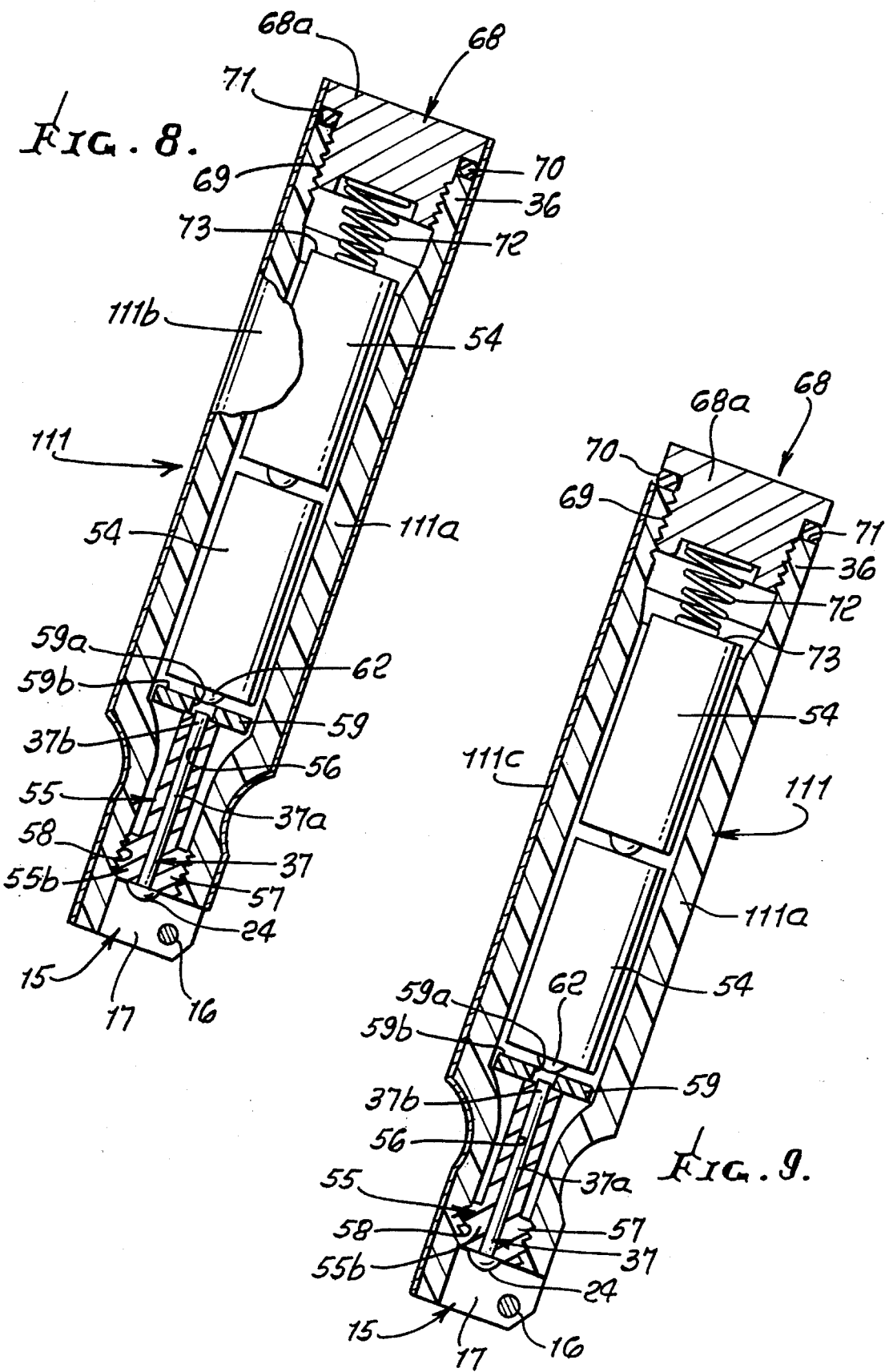

FLUID SUBMERSIBLE LARYNGOSCOPE PREVENTING ELECTROLYTIC CURRENT FLOW

BACKGROUND OF THE INVENTION

This invention generally relates to examining devices such as laryngoscopes and particularly to an improved submersible device of this type.

Laryngoscopes generally comprise a blade and a cooperating handle which are connected together in an L-shaped configuration. The hollow handle normally serves as an enclosure for a power supply such as one or more dry cells which are adapted to energize a light bulb. The light from the bulb passes to the distal end of the blade to illuminate the patient's mouth and larynx during the examination thereof by medical personnel. A surface on the blade is used to press against the tongue and mandible of a patient in a supine position in order to prevent the patient's tongue from obstructing the visual examination of the larynx by medical personnel.

While the instrument is useful for examining the larynx, the primary function of the laryngoscope is to expose the larynx in order to facilitate the insertion of an endotracheal tube. The surface of the laryngoscope blade adjacent the handle is urged against the tongue and mandible to expose the larynx in such procedures and the opposite blade surface is positioned opposing the upper front teeth of the patient.

The handle and blade are desirably re-usable, and must be cleaned thoroughly after use. It is desirable to immerse the handle into cleaning solution; however such solution is typically current conducting, i.e. electrolytic. This results in current flow between an electrical contact at an end of the handle to which the blade is connectible, and the metal handle, producing corrosion and draining the batteries, since immersion continues over extended periods of time. There is need for method and means for preventing such electrolytic current flow, during immersion, and need for an improved, low cost handle.

SUMMARY OF THE INVENTION

It is a major object of the invention to provide a solution to the above problems associated with a fluid or liquid submersible laryngoscope including a hollow handle to contain power supply means, a blade to be inserted into a patient's mouth, and means to removably attach the blade to an end portion of the handle in a substantially L-shaped configuration. The improved handle comprises:

a) a terminal pin carried by the handle at the end of the handle, b) first fluid sealing means between the terminal pin and handle to block access of external fluid into the hollow handle, whether or not the blade is attached to the handle, and when the handle is submerged in fluid, c) and means for preventing deflection of the pin into electrical current transmitting relation with the power supply means until the blade is attached to the handle.

As will appear, the fluid sealing means may typically comprise a tubular elastomeric body carrying the terminal pin, the pin having a shank in fluid sealing relation with a bore defined by said elastomeric body, whereby center extent of the elastomeric body is resiliently yieldable axially of the handle to allow the pin and said center extent of the body to deflect axially when the blade is fully attached to the handle.

Another object comprises the provision of an member located between the power supply means and said first fluid sealing means, and relative to which the pin is movable, endwise. That member may have an aperture into which the pin partially extends; and it may have annular disc-shaped configuration. The terminal pin end typically projects only partly into the aperture, i.e. to remain in spaced relation to a battery end contact or terminal in the housing, whereby only when the L-shaped blade is forcibly connected to the handle is the terminal pin displaced into contact with the battery terminal. Accordingly, no current can flow to the terminal pin when the blade is not connected to the handle.

Other objects include the provision of a terminal pin having a head on the shank projecting endwise outwardly of the elastomeric body, said body having an exterior generally annular surface in fluid sealing engagement with a bore defined by the handle; the provision of an end closure attached to an end of said body remote from the terminal pin, the closure providing one current passing connection between a power source and said pin; the provision of a compression spring urging the power supply means toward the pin, the body being compressible to resiliently transmit force for improved contact of the pin with a surface on the blade, the provision of an end cap removably attached to the end of the handle, remote from the blade, and second fluid sealing means between the cap and handle to block access of external fluid into the hollow handle and the provision of a metallic handle and cap, with a fluid reading 0-ring therebetween.

Yet another object is the provision of a handle consisting primarily of synthetic resinous material. In this regard, the body may have an electrically conductive coating to provide a return current path between the bulb and the power supply means, or battery. Alternatively, electrical leads may be provided externally and internally in the handle body to enable current flow when the blade is connected to the handle, yet prevent current flow when the handle is immersed in cleaning solution.

These and other objects and advantages of the invention, as well as the details of an illustrative embodiment, will be more fully understood from the following specification and drawings.

DRAWING DESCRIPTION

FIG. 1 is a side elevational view of a laryngoscope preparatory to being used on a patient which embodies features of the invention;

FIG. 2 is a perspective enlarged view of the blade of the laryngoscope shown in FIG. 1;

FIG. 3 is a side elevational view partially in section, of the laryngoscope with the blade in a ready position;

FIG. 4 is a partial side elevational view, partially in section, of the laryngoscope with the blade in the operative position;

FIG. 5 is a cross sectional view taken along the lines 5—5 shown in FIG. 4;

FIG. 6 is a cross sectional view of the handle of the prior art;

FIG. 7 is a fragmentary view like that of a portion of FIG. 6.

FIG. 8 shows a handle of the instant invention, the body of which consists of synthetic resin with a thin exterior coating of metal; and FIG. 9 shows a handle like that of FIG. 8, but wherein the metal overcoat is omitted, and other electrical leads are employed.

DETAILED DESCRIPTION

Reference is made to the drawings which illustrate a laryngoscope embodying features of the present invention. The instrument is intended for use by medical personnel in the examination of a patient's mouth and larynx and particularly to expose the larynx to facilitate the insertion of an endotracheal tube. As shown in FIG. 1, the laryngoscope 10, which comprises a handle 11 and blade 12, is utilized to depress the patient's tongue and mandible 13. Frequently, the patient's front teeth 14 are used as a fulcrum for the blade 12 in order to more completely expose the patient's larynx during the examination of the larynx and the insertion of an endotracheal tube.

One form of means used to couple the blade 11 to the handle 12 is illustrated in FIGS. 2–6. As shown therein, the upper end of the handle 11 has an open channel 15, which is provided with a pivot rod 16 extending between flanges 17. The inner side of one flange has a groove or dimple 19 adapted to seat a spring urged detent 20 projecting at one side surface 18 of boot-shaped appendage 22 or the blade.

The boot shaped appendage 22 interfits into the open channel 15 and is mounted therein in a pivotal fashion. The front end 23 of the boot shaped appendage 22 is hooked under the pivot rod 16 during the pivotal mounting thereof, in a conventional fashion. To mount the blade onto the handle 11, the appendage 22 of the blade 12 is inserted into the open top channel 15 with a pivotal motion so that the front end 23 rotates under the pivot rod 16 i.e. from FIG. 3 to FIG. 4 condition. The detent 20 moves into engagement with the groove 19 provided in the surface 18, to thereby snap retainer appendage 22 in firm interfit with the pivot rod 16, as the blade moves from ready position, as shown in FIG. 3, to fixed position seen in FIG. 4.

Preferably, a light switch or contact 24 is provided at the bottom of the channel 15 in a position so that it is activated only when the blade 12 is rotated and locked into an operating position. A light source 25 such as an incandescent bulb is provided on the blade and is energized when the light switch 24 is activated. As shown in FIG. 3, when the blade 12 is initially mounted on the handle 11, the blade 12 is in a ready position on the handle 11 but a contact 26a on the bottom surface 26 of the appendage 22 does not activate, i.e. engage a pin terminal. Further rotation of the blade 12 causes the detent 20 to engage the groove 19, and to thereby lock the blade 12 in an operating position and simultaneously therewith to cause contact 26a to engage, the head 24 of a terminal pin 37, which in turn activates or energizes the light source 25. Wiring 50 extends from contact 26a to the bulb and may include a ground wire 50a returning to engage the metal of channel flange 17 (see FIG. 5). Metal channel 33 on the blade protectively confines wiring 50 and is carried by web 32.

As best shown in FIGS. 2–4, light is directed from the light source 25 to ensure the proper illumination of a patient's mouth and larynx when the laryngoscope is being used. The light, at the proximal end of a light conductor, is located near the end 29 of the blade 12 so that, when the blade 12 is rotated into its final operating position, the contact 26a is immediately adjacent to and engages the terminal 24 so that there is a reliable and efficient electrical coupling therebeteween, to provide electrical energization of the light bulb 25 or light conductor.

The lower portion 30 of the blade 12 which comes in contact with the tongue and mandible 13 of the patient should be rigid, whereas the upper section 31 comes in contact with the patient's teeth 14. Surface 31 which is in contact with the patient's teeth 14 is supported to the rigid portion 30 of the blade 12 by means of the wall or web 32.

The handle 11, which is typically metallic, has an internal cavity 11a which is adapted to hold one or more battery units 54 (see FIG. 6) which supply electrical energy to light source 25.

The handle comprises a tubular body 34 having a reduced diameter end 35, and opposite end 36. The contact 24 is advantageously formed at the head of terminal pin 37 located at handle end 35. The pin is placed in electrical energy transmitting relation with the light source, by means such as that referred to above.

Also provided is first fluid sealing means, located between the terminal pin and handle to block access to external fluid into the hollow handle, whether or not the blade is attached to the handle, and when the handle is submerged in fluid, such as electrolytic cleaning fluid (boric acid, or other). As shown, the first fluid sealing means comprises a tubular elastomeric body 55 carrying the terminal pin, the conductive pin having a shank 37a in fluid sealing relation with a bore 56 defined by the elastomeric body 55, the latter having an exterior generally annular surface 57 in fluid sealing engagement with a bore 58 defined by the metallic handle body. Surfaces 57 and 58 may advantageously be threaded, and be in tight compressive engagement to define a good fluid seal.

Referring to FIG. 8, there is provided means for preventing deflection of the pin 37 and its shank 37a into electrical current transmitting relation with the power supply means, i.e. batteries 54, until the blade 12 is attached to the handle, as described above. Such means may advantageously take the form of an insulative member located between the power supply means and the first fluid sealing means (i.e. body 55), and relative to which the terminal pin is movable endwise. As shown in FIG. 8, the insulative member comprises a synthetic resinous disc 59 having annular configuration about a central aperture or opening 59a into which the pin may partially extend, in spaced relation from battery end contact 62 facing the end 37b of the pin. Elastomeric body 55 is endwise compressible, but prior to such compression, it holds pin shank 37a, and pin end 37b, spaced from the battery contact as seen in FIG. 8. Thus, the handle in FIG. 8 configuration may be placed in electrolytic fluid, and no circuit will be established as no fluid gains access to the space 59a. (If pin 37 did engage the battery contact, the circuit current would flow from 54 to 37, to head 24 and then via the electrolytic liquid to metal body 34, and back to end 73 of the second battery 54, as shown).

When the blade is connected to the handle, blade contact 26a deflects pin head 24 toward the disc 59 to an extent that pin head 37b positively engages battery contact 62. Under these conditions elastomeric body 55 is endwise compressed, and deflected, as shown. Pin end 37b moves endwise in aperture 59a, into proximity to the face 59b of the disc engaged by contact 62 and into engagement with contact 62. This results in establishment of a circuit from 54 through 37 and 24, to the light bulb, as described above. Once the blade is disconnected, the body 55 relaxes and retracts the pin relative to disc 59, to assume the configuration of FIG. 8. Enlarged body section 55b acts as a spring, when deflected, and its exterior seals to threaded bore 58.

An end cap 68 is removably attached to the end 36 of the handle, remote from the blade, and second fluid sealing means is provided between the cap and handle to block access of external fluid into the hollow handle, via end 36. In this regard, the cap may have threaded attachment at 69 to the handle, the cap and handle typically being metallic. Such second fluid sealing means may comprise an elastomeric O-ring 70 compressed between cap flange 68a and handle end 71 to establish a ground. Element 70 may be a rubber washer.

A coil spring 72 is located between the cap 68 and the end 73 of one battery 54, and in FIG. 8, spring 72 may be slightly compressed as end pin 37b pushes against battery contact 62.

After use, the blade is decoupled from the handle by simply rotating the blade 12 toward the handle 11 and then pushing upwardly on the blade 12 to disengage or unhook the front end 12 of appendage 22 from the pivot rod 16. The blade being formed from metal, can be sterilized and reused, as is the handle.

It will be noted that elements 54, 59 and 37 are supported endwise betweeen spring 72 and endwise compressible member 55, whereby floating adjustment of these elements, relative to the blade contact 26a is achieved, and slightly different sized (length) batteries can be employed without deleterious effort. Note also that disc 59 is postitioned by the body 55, the end of which it engages.

FIG. 8 shows a handle 111 like that of FIGS. 1–7 except that it consists of a body 111a of molded synthetic resin (as for example ABS), onto which a thin layer 111b of metal (such as aluminum) has been plated or otherwise applied. This construction greatly reduces the cost of manufacture of the handle.

FIG. 9 shows a handle like that of FIG. 8, except that the exterior plating 111b is not employed; instead, thin electrical leads 111c are locally formed or applied to the body 111a, to establish electrical transmission between coil 72 and the blade body when the blade is attached.

Although specific embodiments of the invention are described herein, in connection with laryngoscopes, it is clear the improved means to connect a blade and a handle into an L-shaped configuration can be employed in other examining devices. FIG. 8 may be regarded as a preferred embodiment.

Modifications and improvements can be made to the present invention without departing from the inventive concepts thereof. One modification is to make the blade of molded plastic (for throw away).

I claim:

1. In a fluid submersible laryngoscope including a hollow handle to contain power supply means, a blade to be inserted into a patient's mouth, and means to removably attach the blade to an end portion of the handle in a substantially L shaped configuration, the improvement comprising:

a) a terminal pin carried by the handle at said end portion of the handle, b) first fluid sealing means between the terminal pin and handle to block access of external fluid into the hollow handle, whether or not the blade is attached to the handle, and when the handle is submerged in fluid, said fluid sealing means comprising a tubular elastomeric body carrying said terminal pin and having an end, and c) means for preventing deflection of the terminal pin into electrical current transmitting relation with the power supply means until the blade is attached to the handle, wherein said means for preventing deflection comprises an insulation disc located between said power supply means and said end of the elastomeric body, said insulation disc defining a bore through which said terminal pin at least partially extends, whereby attachment of the blade to the handle causes said terminal pin to move through said bore into current transmitting relation with the power supply means.

2. The improvement of claim 1 wherein said elastomeric body includes a bore and a center extent that is resiliently yieldable axially of the handle to allow the terminal pin and said center extent of the elastomeric body to deflect axially when the blade is fully attached to the handle, said terminal pin having a shank in fluid sealing and retained relation with said bore.

3. The improvement of claim 2 wherein the terminal pin has a head on the shank projecting endwise outwardly of said elastomeric body, said elastomeric body having an enlarged section and an exterior generally annular surface on said enlarged section in fluid sealing engagement with a bore defined by the handle.

4. The improvement of claim 3 wherein the elastomeric body is in part spaced radially inwardly from the handle and extending axially of the handle between said enlarged section and said power supply means to accommodate deflection.

5. The improvement of claim 1 including an end cap attached to an end of said handle remote from the terminal pin, said cap providing a current passing connection between said power supply means and said terminal pin, and further including a current passing thin layer extending externally of the handle.

6. The improvement of claim 3 including a compression spring urging said power supply means toward the terminal pin.

7. The improvement of claim 2 wherein said elastomeric body and said handle have threaded interconnection.

8. The improvement of claim 1 including an end cap removably attached to the end of the handle, remote from the blade, and second fluid sealing means between the cap and handle to block access of external fluid into the hollow handle.

9. The improvement of claim 8 wherein the handle and end cap are metallic, and said second fluid sealing means comprises an elastomeric O-ring.

10. The improvement of claim 4 wherein the blade consists of the synthetic resinous material, and has a bite flange thereon.

11. The improvement of claim 1 wherein a bulb is carried by the blade near the end thereof remote from the handle.

12. The improvement of claim 5 wherein the handle consists primarily of synthetic resinous material.

13. The improvement of claim 12 wherein the current passing thin layer is an electrically conductive coating on the handle to provide a return current path.

* * * * *